United States Patent [19]

Raines

[11] 4,244,366
[45] Jan. 13, 1981

[54] SYRINGE STROKE CONTROLLING MECHANISM

[75] Inventor: Kenneth Raines, Bethlehem, Pa.
[73] Assignee: Burron Medical, Inc., Bethlehem, Pa.
[21] Appl. No.: 89,365
[22] Filed: Oct. 30, 1979
[51] Int. Cl.$^3$ .............................................. A61M 5/00
[52] U.S. Cl. ........................... 128/218 PA; 128/218 C
[58] Field of Search ......... 128/218 PA, 218 P, 218 R, 128/218 C, 213, 215, 216, 234

[56] References Cited

U.S. PATENT DOCUMENTS

| 2,823,674 | 2/1958 | Yochem | 128/218 C |
| 2,863,452 | 12/1958 | Ogle, Sr. | 128/218 C |
| 3,122,280 | 2/1964 | Goda | 128/218 C |

FOREIGN PATENT DOCUMENTS 814536 9/1945 France .................................. 128/218 C

*Primary Examiner*—John D. Yasko
*Attorney, Agent, or Firm*—Shoemaker and Mattare, Ltd.

[57] ABSTRACT

A syringe stroke controlling mechanism includes a gripping member encircling a syringe barrel and a cap on the plunger of the syringe. A spring urges the plunger outwardly of the barrel and a metering rod couples the cap to the gripping member. Adjustment of the metering rod sets the maximum separation permitted between the plunger cap and the gripping member and thereby controls the stroke of the syringe plunger.

12 Claims, 7 Drawing Figures

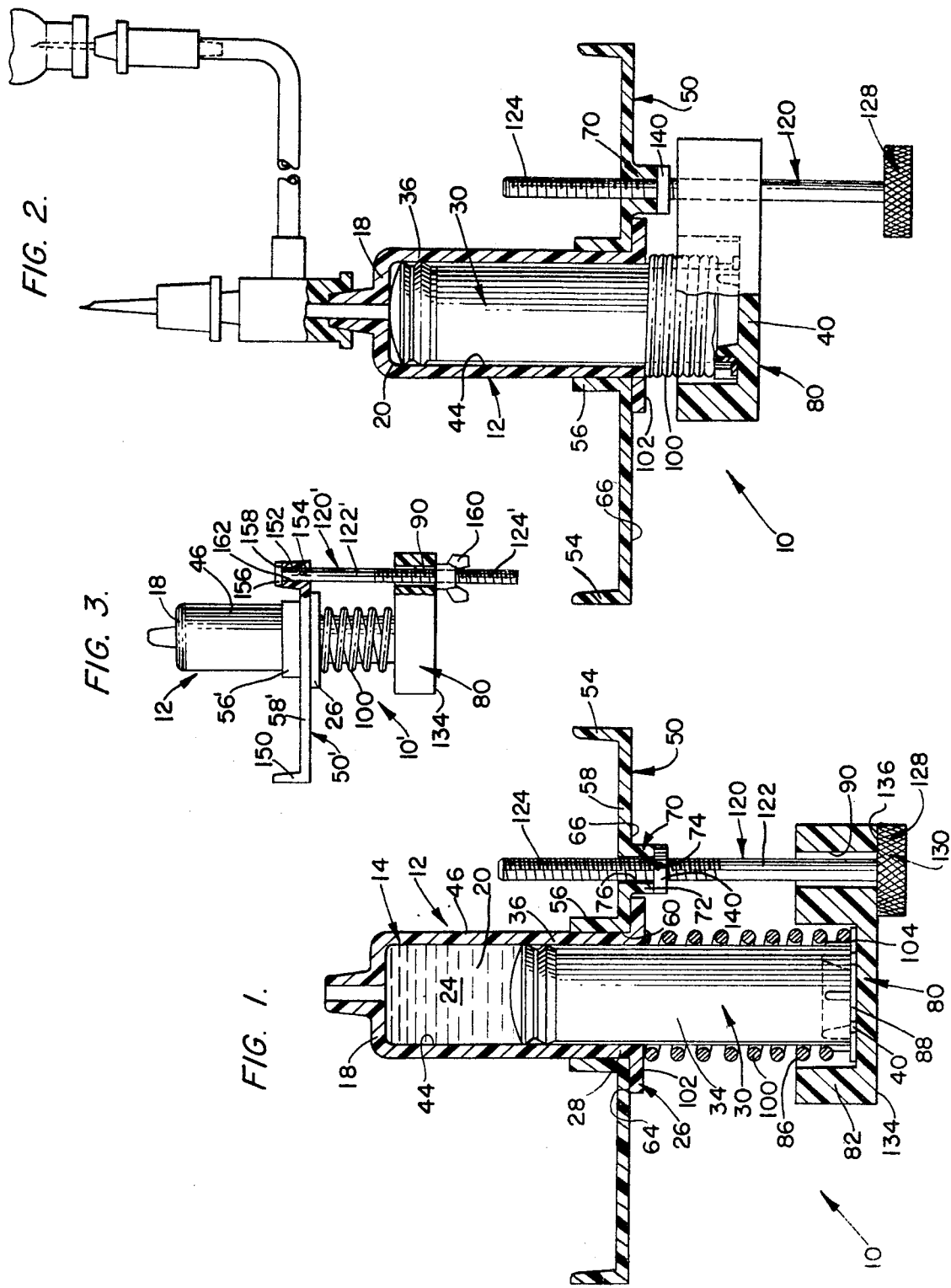

SYRINGE STROKE CONTROLLING MECHANISM

BACKGROUND OF THE INVENTION

The present invention relates in general to syringes, and, more particularly, to dosage regulators used with syringes.

In many applications, repeated dosages of medicament must be measured. In hospitals, or the like, such repeated dosages are often measured by reusable syringes because of the accuracy possible using such syringes.

In order to insure extreme precision, the syringe used to define such dosages has some means for accurately setting and precisely regulating such dosages. Known dosage regulating means are either complicated to assemble and use, very expensive, or the like.

Thus, there is need for a dosage regulator for use in a disposable syringe which is inexpensive and easy to manufacture, set up and use, yet can be accurately set and will precisely control dosage size.

SUMMARY OF THE INVENTION

The dosage regulator embodying the teachings of the present invention is used with a disposable syringe.

The device includes a molded finger grip extension element which serves as a gripping member and which accommodates the syringe barrel. A cap element releasably accommodates the plunger head. A compression spring urges the plunger outwardly of the syringe barrel, and a threaded metering rod couples the plunger head accommodating cap to the syringe barrel accommodating gripping member.

The metering rod is used to adjust the amount of volume set by the plunger in the syringe barrel by controlling the amount of separation permitted between the plunger head and the barrel.

The device is intended for use in repetitive fluid dispensing procedures. After depressing or releasing the syringe plunger, the spring biases the plunger outwardly of the syringe barrel until that plunger is stopped by a plunger stop adjustment mechanism located outwardly of the syringe barrel flange.

The operation of the device is as follows: an adjustment member is turned to set the distance permitted for the stroke of the plunger; the plunger is depressed to inject fluid; the plunger is released and the spring returns that released plunger to a position with respect to the syringe barrel which has been preset by the adjustment of the metering rod. The metring rod remains fixed during the just-discussed process, and the cap member slides on that fixed metering rod.

OBJECTS OF THE INVENTION

It is, accordingly, a main object of the present invention to provide a syringe stroke controlling mechanism which is easily manufactured.

It is another object of the present invention to provide a syringe stroke controlling mechanism which is easily set up and used.

It is yet another object of the present invention to provide a syringe stroke controlling mechanism which is amenable for use in a wide variety of applications.

These together with other objects and advantages which will become subsequently apparent reside in the details of construction and operation as more fully hereinafter described and claimed, reference being had to the accompanying drawings forming part hereof, wherein like reference numerals refer to like parts throughout.

BRIEF DESCRIPTION OF THE DRAWINGS

FIG. 1 is an elevation view of a syringe having the device embodying the teachings of the present invention thereon with the plunger of the syringe in the outermost position.

FIG. 2 is an elevation view of a syringe having the device embodying the teachings of the present invention thereon with the plunger of the syringe in the fully depressed position.

FIG. 3 is an elevation view of an alternative embodiment of a syringe having the device embodying the teachings of the present invention thereon with the plunger of the syringe in the fully depressed position.

DETAILED DESCRIPTION OF THE INVENTION

Figure 4:
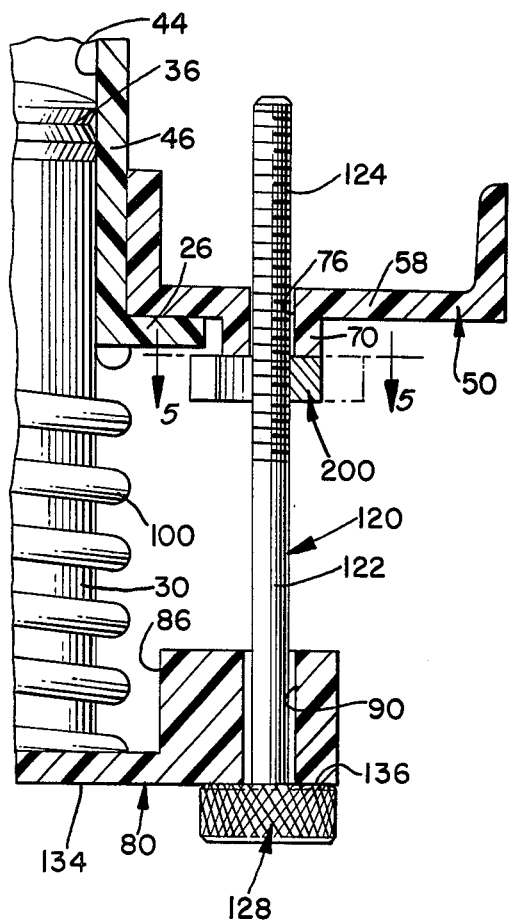
FIG. 4 is an elevation view of an alternative embodiment of the present invention.

Shown in FIGS. 1 and 2 is a syringe stroke controlling mechanism 10 for regulating the volume of fluid in a charge associated with a reusable syringe 12. The syringe 12 includes a tubular barrel 14 having a male luer-taper 16 mounted on a first end thereof, which hereinafter will be referred to as forward end 18. The luer-taper is used to receive and dispense fluid through a dual-check valve attached to a solution set and container or the like. The tubular barrel 14 has a fluid containing bore 20 defined therein, and fluid 24, such as medicament, or the like, is contained therein. A finger grip 26 is integrally mounted on the end of the barrel remote from the forward end, which hereinafter will be referred to as rear end 28, and a plunger 30 is slidably received in the barrel. The plunger 30 includes a plunger rod 34 having a stopper 36 on one end thereof and a plunger head 40 on the other end thereof. The stopper 36 is sized to produce a sliding fluid seal with inner surface 44 of barrel wall 46 for moving fluid into and out of the syringe via the cannula. The syringe 12 is operated in the usual manner for receiving and/or dispensing fluid, and is intended for repeated uses.

The dosage received and/or dispensed by the reusable syringe is regulated by the stroke controlling mechanism 10 which controls the length of the plunger stroke with respect to the tubular barrel 14. As seen in the figures, the length of a plunger stroke determines the volume of fluid in a charge contained in the syringe barrel. As will occur to those skilled in this art, accurate dosage is important for many reasons and applications.

The stroke controlling mechanism 10 includes an annular finger hold extension or handle grip 50 circumferentially surrounding the barrel wall 46. The handle grip 50 serves to anchor the mechanism 10 to the syringe and to provide a comfortable grip for a user.

The handle grip 50 includes a pair of circumferntially disposed, depending skirts 54 and 56 integrally attached to a land 58. The depending skirt 56 defines a syringe barrel receiving bore 60 which snugly receives the syringe barrel. The syringe finger grip 26 has undersurface 64 thereof aabuttingly mounted on top surface 66 of the land 58. The depending skirts extend longitudinally and axially of the tubular syringe barrel 14, and the skirt 56 is long enough to securely mount the barrel in the bore 60 and prevent twisting and tilting of the syringe with respect to the handle grip during use.

The bore 60 is shown in the figures as being centrally disposed on the handle grip, but can be offset to provide comfort for a user. Thus, land 58 can have unequal lands located on diametrically opposite sides of the syringe barrel which have different sizes to comfortably receive, for example, a user's index finger on one land, and a user's middle and ring finger on the other land.

An annular boss member 70 is located closely adjacent the bore 60 and includes a wall 72 standing proud of the land top surface 66 and a bore 74 defined by that wall extending through the handle grip and being axially parallel with the longitudinal axis of the syringe barrel. The wall 72 is integral with the handle grip. The boss 70 includes threads 76 located internally of the bore 74 for a purpose to be discussed below.

An integral cap member 80 is positioned on the syringe plunger head, and includes a housing 82 having a blind-ended bore 86 defined therein for releasably receiving the syringe plunger head 40 in a gripping member 88 which is fixed to the cap member within the bore 86. A metering rod bore 90 is defined through the cap member 80 adjacent the bore 86. Both bores 86 and 90 extend in a common direction, and, in the assembled unit, will be coaxial with the syringe barrel. In fact, the longitudinal axis of the bore 86 will preferably be coincident with the longitudinal axis of the syringe barrel in the assembled unit, and the longitudinal axis of the bore 90 will preferably be coincident with the longitudinal axis of the bore 74.

A helical compression spring 100 is seated at one end thereof on top surface 102 of the finger grip 26 and at the other end thereof on undersurface 104 of the plunger head 40. The spring is compressed to be biased longitudinally of the syringe so that head 40 is yieldably urged away from the barrel 14. With the spring 100 in place, the plunger 30 is depressed into the FIG. 2 configuration against the bias of the spring, and when depressing force is released from the plunger, the spring urges and returns the plunger into the FIG. 1 configuration.

A metering rod 120 is received in the aligned bores 74 and 90. The rod includes a shaft 122 having screw threads 124 on one end thereof and an adjusting knob 128 on the other end thereof. The adjusting knob has knurling 130 on the outer circumferential surface thereof for providing a secure gripping surface.

As best shown in FIG. 1, the metering rod is freely slidably received in the bore 90, and the threads 124 are cooperably received by the threads 76 located internally of the bore 74 to threadably and adjustably lock the metering rod to the handle grip 50.

The spring 100 urges the cap member 80 rearwardly of the syringe, and top surface 134 of the cap member abuts lower surface 136 of the adjusting knob to thereby couple the cap member to the hand grip via the metering rod.

As shown in FIG. 2, the sliding attachment of the metering rod to the cap member permits the cap member, and plunger, to be depressed toward the syringe barrel while the metering rod remains fixed and stationary with respect to that syringe barrel. Releasing depressing force from the cap member permits the spring 100 to return the cap member, and plunger, to the position shown in FIG. 1. The travel of the plunger with respect to the syringe barrel is thus controlled by the metering rod.

As can be seen in the figures, the threads 124 on the metering rod extend from the terminal end of that rod to a location between that terminal end and the adjusting knob. By rotating the metering rod, the distance between the handle grip and the cap member is adjusted by adjustment of the amount of takeup of the threads 124 and the threads 76 of the boss member. Due to the rearward bias of the spring 100, this takeup adjusts the at-rest position of the plunger in the syringe barrel. The at-rest position is shown in FIG. 1, and thus the amount of takeup set on the metering rod adjusts the size of the dosage contained in the syringe.

An annular washer 140 can be mounted on the top of the boss member if desired. The washer can have internal threads which cooperate with the metering rod threads so that the boss member need not have internal threads. Of course, both elements can be internally threaded if so desired.

The handle grip 50 and the cap member 80 are molded elements which are each individually molded as single pieces. Preferably, plastic-type material is used for these elements.

The cooperating threads on the metering rod assembly can have any size so that extremely fine adjustments can be made to the setting of that metering rod. In fact, metering rods and washers can have several different thread sizes so that if more precision is required than is provided by a particular metering rod, a different controller can be substituted therefor.

An alternative embodiment of the syringe stroke controlling mechanism is shown in FIG. 3, and is denoted by the reference numeral 10'. The mechanism 10' includes an annular finger hold extension or handle grip 50' circumferentially surrounding the barrel wall 46 of the syringe.

The handle grip includes circumferentially disposed depending skirts 150 and 56' integrally attached to a land 58'. The skirt 56' is similar to the skirt 56, and will not be further discussed.

The skirt 150 includes a boss 152 which has a bore 154 defined therein to extend in the longitudinal direction of the syringe barrel. The boss 152 can be cylindrical or tapered. The boss 152 is located so that the bore 154 is axially aligned with the bore 90 of the cap member 80 positioned on the syringe plunger head.

A metering rod 120' is received in the aligned bores 90 and 152. The rod 120' includes a shaft 122' having screw threads 124' on one end thereof and a head 156 on the other end thereof. The screw threaded end of the metering rod 120' is freely slidably received in the cap located bore 90, and the head 156 is in contact with lower rim 158 of the boss 152. The head is in abutting contact with that rim and can be fixed to that rim if so desired. A threaded fastener, such as a wing nut 160, is threaded onto the threads 124' and abuts upper surface 134 of the cap member 80.

The metering rod 120' couples the handle grip 50' to the cap member 80, and the fastener 160 is operated to adjust the amount of compression to be set on the spring 100 as in the other embodiments of the syringe stroke controlling mechanism. The metering rod 120' remains stationary with respect to the syringe during the stroke of the syringe plunger, and the spring 100 urges the cap member against the fastener 160 at one end of the stroke. By rotating the fastener 160 on the metering rod 120', the length of the plunger stroke is controlled, and hence the size of the dosage contained in the syringe is regulated.

The metering rod head end can include a threaded head which is threaded into threads defined in the internal surface 162 of the bore 154.

Figure 5:
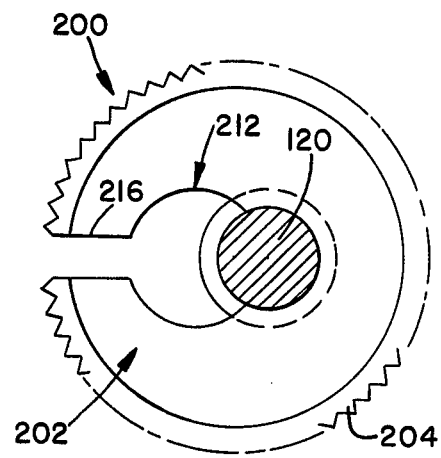
FIG. 5 is a view taken along line 5—5 of FIG. 4 showing the device in a thread engaged position.
Figure 6:
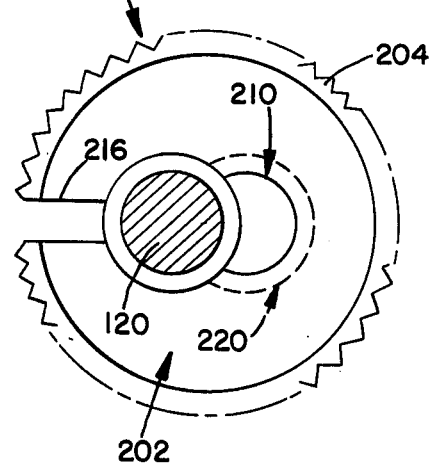
FIG. 6 is a view similar to FIG. 5 showing the device in a thread disengaged position.
Figure 7:
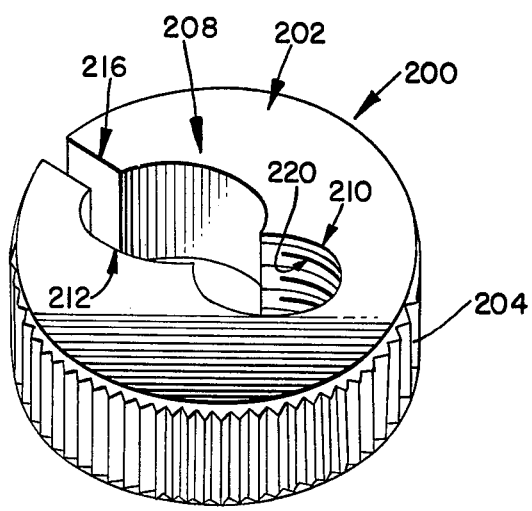
FIG. 7 is a perspective of the alternative device embodying the teachings of the present invention.

Yet another alternative embodiment of the present invention is shown in FIGS. 4-7. A fastener 200 is mounted on boss member 70. The fastener 200 is shown in FIGS. 5-7 to include a nut 202 having a circular periphery with knurling 204 on the side thereof to provide a gripping surface.

The nut 202 has a figure eight shaped slot 208 defined therethrough which includes a small opening 210 and a large opening 212 joined to form the figure eight configuration. A slot 216 connects the periphery of the nut to the large opening.

The small opening includes threads 220 defined internally of the opening, and has a diameter sized so that the threads 220 can engage the threads 124 of the metering rod. The large opening has a diameter large enough to permit free sliding of the metering rod therein, in a manner similar to the free sliding movement of the metering rod permitted by the bore 90 in the cap member 80.

The fastener 200 will permit rapid stroke adjustment while retaining the fine adjustment feature thereof.

To adjust the syringe stroke, the syringe plunger is depressed to a desired level, the nut 202 is disengaged by "snapping" it off of the metering rod. It is noted that in the FIG. 4 form, he nut remains on the rod, and the rod enters the non-threaded hole 212 for the gross adjustment. The nut is moved to execute the gross adjustment, and snapped back onto the threaded rod so that the threads 220 engage the threads 124 of the metering rod. Fine adjustments of the plunger position are made by turning the nut with the threads 220 and 124 engaged.

The FIG. 4 form of this embodiment shows the nut 202 slidably mounted on the boss member 70. Several forms of fastening means can be used to accomplish this movable mounting. For example, engaged keys and keyways on the abutting surfaces of the nut and boss member can be used, mounting jackets, mounting straps and stops, and the like, can be used. Alternatively, the nut can be stationary, and the metering rod moved, in which case the bore 90 will have a diameter larger than that shown in FIG. 4, and large enough to permit such rod movement toward and away from the plunger 30. The head 128, of course, remains larger than the bore 90 to remain operatively engaged with top surfaces 134 of cap member 80.

Preferably, the nut 202 is nylon, and hence flexible enough to permit the afore-discussed movement of the metering rod between the openings 210 and 212 while being rigid enough to securely hold the threadably engaged rod and nut in place.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:
1. A stroke controlling mechanism for use on a reusable syringe having a forward end and a rearward end, said stroke controlling mechanism comprising:

a molded gripping member having a syringe barrel bore defined therein for snugly receiving a syringe barrel portion, said gripping member having a flange surrounding said bore for contacting the syringe barrel to hold such syringe securely in position with respect to said gripping member, said gripping member being in abutting contact with finger grip means of a syringe so that said syringe finger grip means prevents said gripping means from moving rearwardly off the syringe barrel;

a molded cap member having a plunger head bore defined therein for receiving a syringe plunger head;

a compression spring surrounding a syringe plunger and located between said cap member and said gripping member, said compression spring being positioned and sized to urge the syringe plunger outwardly of a syringe barrel;

a gripping member metering rod bore defined in said gripping member adjacent said syringe barrel bore;

a cap member metering rod bore defined in said cap member adjacent said plunger head bore to be in axial alignment with said gripping member metering rod bore;

threaded means on said gripping member metering rod bore;

a metering rod received in said axially aligned metering rod bores, said metering rod having an adjusting knob on one end thereof and threads on the other end thereof, said metering rod threads cooperating with said threaded means and said adjusting knob abutting said cap member to couple said cap member to said gripping member in a manner which resists the urging of said spring against the plunger, said metering rod being threadably received in said threaded means and freely slidably received in said cap member metering rod bore for adjusting the maximum distance permitted between said plunger head and said barrel for adjusting dosage size associated with a syringe.

2. The stroke controlling mechanism defined in claim 1 further including a boss member surrounding said gripping member metering rod bore.

3. The stroke controlling mechanism defined in claim 2 further including an internally threaded washer mounted in said boss member.

4. The stroke controlling mechanism defined in claim 3 further including knurling on said adjusting knob.

5. The stroke controlling mechanism defined in claim 4 further including a peripheral skirt surrounding said gripping member.

6. The stroke controlling mechanism defined in claim 5 wherein said gripping member and said cap member are formed of plastics type material.

7. A stroke controlling mechanism for use on a reusable syringe having a forward end and a rearward end, said stroke controlling mechanism comprising:

a molded gripping member having a syringe barrel bore defined therein for snugly receiving a syringe barrel portion, said gripping member having a flange surrounding said bore for contacting the syringe barrel to hold such syringe securely in position with respect to said gripping member, said gripping member being in abutting contact with finger grip means of a syringe so that said syringe finger grip means prevents said gripping means from moving rearwardly off the syringe barrel;

a molded cap member having a plunger head bore defined therein for receiving a syringe plunger head;

a compression spring surrounding a syringe plunger and located between said cap member and said gripping member, said compression spring being positioned and sized to urge the syringe plunger outwardly of a syringe barrel;

a gripping member metering rod bore defined in said gripping member adjacent said syringe barrel bore;

a cap member metering rod bore defined in said cap member adjacent said plunger head bore to be in axial alignment with said gripping member metering rod bore;

a metering rod received in said axially aligned metering rod bores, said metering rod having a head on one end thereof and threads on the other end thereof;

a threaded means cooperating with said metering rod threads, said metering rod head contacting one of said gripping member or said cap member and said threaded means contacting the other of said gripping member and said cap member to couple said cap member to said gripping member in a manner which resists the urging of said spring against the plunger, said metering rod being threadably received in said threaded means and freely slidably received in said cap member metering rod bore for adjusting the maximum distance permitted between said plunger head and said barrel for adjusting dosage size associated with a syringe.

8. The stroke controlling mechanism defined in claim 7 wherein said threaded means includes a wing nut.

9. The stroke controlling mechanism defined in claim 7 wherein said metering rod head abuts a boss on said molded gripping member and said threaded member abuts said cap member.

10. The stroke controlling mechanism defined in claim 1 wherein said threaded means includes a nut having a first threaded opening for threadably receiving said metering rod threads and a second opening sized to permit free sliding of said metering rod through said second opening, said first and second openings being connected so that said metering rod can be moved from one of said openings to the other.

11. The stroke controlling mechanism defined in claim 10 further including knurling on said nut.

12. The stroke controlling mechanism defined in claim 10 wherein said nut is made of a nylon material.

* * * * *